US009609885B2

(12) United States Patent
Diguet et al.

(10) Patent No.: US 9,609,885 B2
(45) Date of Patent: *Apr. 4, 2017

(54) COATING SYSTEM

(71) Applicant: DSM IP ASSETS B.V., Heerlen (NL)

(72) Inventors: Sylvain Diguet, Basel (CH); Bruno H. Leuenberger, Basel (CH); Fabien Laboulfie, Toulouse (FR); Mehrdji Hemati, Toulouse (FR)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/349,258

(22) PCT Filed: Oct. 11, 2012

(86) PCT No.: PCT/EP2012/070119
§ 371 (c)(1),
(2) Date: Apr. 2, 2014

(87) PCT Pub. No.: WO2013/053793
PCT Pub. Date: Apr. 18, 2013

(65) Prior Publication Data
US 2014/0242179 A1    Aug. 28, 2014

(30) Foreign Application Priority Data
Oct. 14, 2011 (EP) .................... 11185187

(51) Int. Cl.
A61K 9/28       (2006.01)
A23L 1/00       (2006.01)
A61K 9/50       (2006.01)
A61K 9/20       (2006.01)
A61K 31/07      (2006.01)
A61K 31/20      (2006.01)
A23K 40/30      (2016.01)
A23K 20/174     (2016.01)
A23K 20/179     (2016.01)
A23K 20/158     (2016.01)
A23P 10/30      (2016.01)
A23P 20/10      (2016.01)
A23L 29/10      (2016.01)
A23L 33/105     (2016.01)
A23L 33/115     (2016.01)
A23L 33/12      (2016.01)
A23L 33/15      (2016.01)
A23L 33/155     (2016.01)

(52) U.S. Cl.
CPC .......... *A23L 1/0055* (2013.01); *A23K 20/158* (2016.05); *A23K 20/174* (2016.05); *A23K 20/179* (2016.05); *A23K 40/30* (2016.05); *A23L 29/10* (2016.08); *A23L 33/105* (2016.08); *A23L 33/115* (2016.08); *A23L 33/12* (2016.08); *A23L 33/15* (2016.08); *A23L 33/155* (2016.08); *A23P 10/30* (2016.08); *A23P 20/11* (2016.08); *A61K 9/2013* (2013.01); *A61K 9/5015* (2013.01); *A61K 9/5036* (2013.01); *A61K 9/5042* (2013.01); *A61K 31/07* (2013.01); *A61K 31/20* (2013.01); *A61K 9/5031* (2013.01)

(58) Field of Classification Search
CPC ...... A61K 9/28; A61K 9/2806; A61K 9/2813; A61K 9/282; A61K 9/2826; A61K 9/2866; A61K 9/2893
USPC .......................................... 424/424, 474–484
See application file for complete search history.

(56) References Cited

U.S. PATENT DOCUMENTS 5,470,581 A  * 11/1995 Grillo .................. A01C 1/06
                                                    424/459
9,200,164 B2 * 12/2015 Diguet ................ A61K 9/2853
2006/0110494 A1   5/2006 Dusterhoft et al.
2007/0104778 A1*  5/2007 Zeng .................. A61K 9/1075
                                                    424/451
2008/0305173 A1  12/2008 Bogue

FOREIGN PATENT DOCUMENTS

CN      88102851 A      12/1988
CN     101176567 A       5/2008
EP       1 413 202       4/2004
WO    WO 2007/070082     6/2007
WO    WO 2008/088776     7/2008

OTHER PUBLICATIONS

International Search Report for PCT/EP2012/070119 mailed Mar. 20, 2013.

* cited by examiner

*Primary Examiner* — Micah-Paul Young
(74) *Attorney, Agent, or Firm* — Nixon & Vanderhye P.C.

(57) ABSTRACT

The present patent application relates to a novel coating system, coated compositions with such a coating system, as well as to the use of such compositions in the production food, feed, dietary supplements and/or pharmaceutical products, as well as to food, feed, dietary supplements and/or pharmaceutical products comprising such compositions.

20 Claims, No Drawings

COATING SYSTEM

This application is the U.S. national phase of International Application No. PCT/EP2012/070119 filed 11 Oct. 2012 which designated the U.S. and claims priority to EP 11185187.9 filed 14 Oct. 2011, the entire contents of each of which are hereby incorporated by reference.

The present patent application relates to a novel coating system, wherein the coating comprises at least one lipid compound and at least one gum having emulsifying properties and at least one film forming compound, characterised in that the lipid compound has a mass median diameter (MMD) of less than 1 µm. Furthermore it relates to compositions coated with such a coating system and the use of such compositions in the production of food, feed, dietary supplements and/or pharmaceutical products.

The goal of the present invention was to find a coating system, which improves the properties of the active ingredient(s), which are coated by such a coating system.

Surprisingly, it was found out that by using a coating system comprising
 (i) at least one lipid compound and
 (ii) at least one gum having emulsifying properties, and
 (iii) at least one film forming compound and/or at least one emulsifier,
characterised in that the mass median diameter of the lipid compound is less than 1 µm,
improved coated compositions are obtained.

The compositions coated by a coating system according to the present invention are improved in regard to
 (a) storage stability;
 (b) sensory (smell and odour); (this is crucial when a strong tasting active ingredient is used);
 (c) control release of the active ingredient.

Therefore the present invention relates to a coating system comprising
 (i) at least one lipid compound and
 (ii) at least one gum having emulsifying properties, and
 (iii) at least one film forming compound and/or at least one emulsifier,
characterised in that the mass median diameter of the lipid compound is less than 1 µm.

Mass Median Diameter or "MMD" is a measurement of the average particle size distribution. The results are expressed as diameters of the total volume distribution at 50% total throughflow. The mass median diameters (MMD) given in the present patent application are measured by using a Malvern Mastersizer 2000. The mean diameter (MD) is measured by using a Coulter N4 Plus. It is to be said that all particle sizes given in this patent application are average particles sizes. Monodispersity of the particles is not an essential criterion of the present invention.

The MMD of the lipid compound used in the coating of the composition according to the invention is less than 1 µm. Preferably, the MMD is below 0.95 µm, more preferably below 0.8 µm.

Preferably for all compositions in this patent application the d50 (measured by a Malvern Mastersizer 200 with Ultrasound) of the lipid compound, most preferably stearic acid, (in the suspension) is 0.10-0.30 µm.

Preferred lipid compounds according to the present invention are saturated fatty acids as well as salts thereof, more preferred stearic acid or palmitic acid, as well as their salts. It is clear that one single lipid compound can be used as well as mixtures of two and more lipid compounds.

The coating system comprises at least one gum having emulsifying properties. Emulsifying properties are such, which allow to producing oil-in-water emulsions. A gum in the context of the present invention is a viscous substance that is extruded by certain plants and trees harden on exposure to air and dry into water-soluble, non crystalline, brittle solids or viscous mass.

Suitable gums according to the present invention are gum acacia, gum ghatti and tic gums. These gums are also the preferred gums.

More preferred is gum acacia.

Therefore the present invention relates to a coating system comprising
 (i) at least one lipid compound and
 (ii) at least one gum chosen from the group consisting of gum acacia, gum ghatti and tic gums, and
 (iii) at least one film forming compound and/or at least one emulsifier,
characterised in that the mass median diameter of the lipid compound is less than 1 µm.

Preferred film forming compounds according to the present invention are hydrocolloids. The hydrocolloid can be either a polysaccharide or a protein. The term polysaccharides includes gums (alginates, pectins, guar, caroube, xanthan), wherein the gums having emulsifying properties are excluded, starches and modified starches, cellulose and cellulose derivatives like carboxymethylcellulose or hydroxypropylmethylcellulose. It is clear that one single film forming compound can be used as well as mixtures of two and more film forming compounds.

Preferred emulsifiers according to the present invention are sucrose ester, ascorbyl palmitate, polyoxyethylene-sorbitan-fatty acid esters (available under the trade name Tween). It is clear that one single emulsifier can be used as well as mixtures of two and more emulsifiers.

Therefore a preferred embodiment of the present invention relates to a coating system comprising
 (i) at least one lipid compound chosen from the group consisting of stearic acid or palmitic acid, as well as their salts and
 (ii) at least one gum chosen from the group consisting of gum acacia, gum ghatti and tic gums, and
 (iii) at least one film forming compound and/or at least one emulsifier chosen from the group consisting of alginates, pectins, guar gum, caroube gum, xanthan, starches, modified starches, cellulose, cellulose derivatives (like carboxymethylcellulose or hydroxypropylmethylcellulose), sucrose ester, ascorbyl palmitate and polyoxyethylene-sorbitan-fatty acid esters,
characterised in that the mass median diameter of the lipid compound is less than 1 µm.

Optionally, the coating system according to the present invention also comprises at least one plasticizer.

Preferred plasticizers according to the present invention are sugars like sucrose or a sugar derivative (mannitol, sorbitol), glycerol, mono- and diglyceride, acetylated monoglyceride, polyethylene glycol (PEG), polypropylene glycol. Preferably the PEG has a molecular weight between 200 and 6000. It is clear that one single plasticizer can be used as well as mixtures of two and more plasticizers.

Therefore the present invention also relates to a coating system comprising
 (i) at least one lipid compound chosen from the group consisting of stearic acid or palmitic acid, as well as their salts and
 (ii) at least one gum chosen from the group consisting of gum acacia, gum ghatti and tic gums, and
 (iii) at least one film forming compound and/or at least one emulsifier chosen from the group consisting of alginates, pectins, guar gum, caroube gum, xanthan, starches, modified starches, cellulose, cellulose derivatives (like carboxymethylcellulose or hydroxypropylmethylcellulose), sucrose ester, ascorbyl palmitate and polyoxyethylene-sorbitan-fatty acid esters, and (iv) at least one plasticizer chosen from the group consisting of sugars (like sucrose), derivatives (mannitol, sorbitol), glycerol, mono- and diglyceride, acetylated monoglyceride, polyethylene glycol (PEG) and polypropylene glycol, characterised in that the mass median diameter of the lipid compound is less than 1 µm.

The coating system can optionally comprise further components. These components can be useful for the production of the coating, the production of the coated composition, the production of the food, feed, dietary supplement or pharmaceutical product, or it can be added for other reasons. Such components can be e.g. dyestuffs, antioxidants, fillers, pH buffers, taste masking substances, etc. If present, such ingredients are used in an amount of up to 5 weight-percent (wt-%), based on the total weight of the coating system (preferably 0.5 to 5 wt-%).

The coating system according to present invention preferably comprises 10 to 50 wt-% of at least one lipid compound, preferably, 20 to 40 wt-%, based on the total weight of the coating system.

The coating system according to present invention preferably comprises 5 to 30 wt-% of at least one gum having emulsifying properties, preferably 10 to 25 wt-%, based on the total weight of the coating system.

The coating system according to present invention preferably comprises 40 to 80 wt-%, preferably 45 to 70 wt-% of at least one film forming compound and/or at least one emulsifier, based on the total weight of the coating system.

It is obvious that the sum of the above mentioned percentages of the coating system always adds up to 100.

Therefore a preferred embodiment of the present invention also relates to a coating system comprising (i) 10 to 50 wt-%, based on the total weight of the coating system, of at least one lipid compound chosen from the group consisting of stearic acid or palmitic acid, as well as their salts and (ii) 5 to 30 wt-%, based on the total weight of the coating system, of at least one gum chosen from the group consisting of gum acacia, gum ghatti and tic gums, and (iii) 40 to 80 wt-%, based on the total weight of the coating system, of at least one film forming compound and/or at least one emulsifier chosen from the group consisting of alginates, pectins, guar gum, caroube gum, xanthan, starches, modified starches, cellulose, cellulose derivatives (like carboxymethylcellulose or hydroxypropylmethylcellulose), sucrose ester, ascorbyl palmitate and polyoxyethylene-sorbitan-fatty acid esters, characterised in that the mass median diameter of the lipid compound is less than 1 µm.

Therefore the present invention also relates to a coating system comprising (i) 10 to 50 wt-%, based on the total weight of the coating system, of at least one lipid compound chosen from the group consisting of stearic acid or palmitic acid, as well as their salts and (ii) 5 to 30 wt-%, based on the total weight of the coating system, of at least one gum chosen from the group consisting of gum acacia, gum ghatti and tic gums, and (iii) 40 to 80 wt-%, based on the total weight of the coating system, of at least one film forming compound and/or at least one emulsifier chosen from the group consisting of alginates, pectins, guar gum, caroube gum, xanthan, starches, modified starches, cellulose, cellulose derivatives (like carboxymethylcellulose or hydroxypropylmethylcellulose), sucrose ester, ascorbyl palmitate and polyoxyethylene-sorbitan-fatty acid esters, and optionally (iv) 5 to 20 wt-%, based on the total weight of the coating system, of at least one plasticizer chosen from the group consisting of sugars (like sucrose), derivatives (mannitol, sorbitol), glycerol, mono- and diglyceride, acetylated monoglyceride, polyethylene glycol (PEG) and polypropylene glycol, and optionally (v) up to 5 wt-%, based on the total weight of the coating system, of at least one further ingredient chosen from the group consisting of dyestuffs, antioxidants, fillers, pH buffers and taste masking substances, characterised in that the mass median diameter of the lipid compound is less than 1 µm.

A coating system according to the present invention is used for coating an active ingredient (or a formulation comprising at least one active ingredient). Such a coated system comprises a core (comprising the active ingredient) and the coating system. The active ingredient which is coated is a fat soluble compound.

Therefore the present invention also relates to a composition comprising (a) a core, wherein the core comprises at least one fat soluble compound and (b) a coating system, comprising
 (i) at least one lipid compound and
 (ii) at least one gum chosen from the group consisting of gum acacia, gum ghatti and tic gums, and
 (iii) at least one film forming compound and/or at least one emulsifier, characterised in that the mass median diameter of the lipid compound is less than 1 µm.

All the preferences for the coating system apply to the above mentioned compositions.

At least one fat soluble compound is coated by the coating system according to the present invention. Preferably the fat soluble compound is a fat soluble vitamin (or vitamin derivate), such as vitamin A or its esters (for example vitamin A acetate and vitamin A palmitate), vitamin E or its esters (for example vitamin E acetate), vitamin K (phytomenadione) and vitamin D3 (cholecalciferol), a PUFA (Poly Unsaturated Fatty Acid) or a carotenoid (such as α- or β-carotene, 8'-apo-β-carotenal, 8'-apo-β-carotenoic acid esters, canthaxanthin, astaxanthin, lycopene, lutein, zeaxanthin or crocetin). Most preferred the fat soluble compound is a vitamin, such as vitamin A or its esters (for example vitamin A acetate and vitamin A palmitate), vitamin E or its esters (for example vitamin E acetate), vitamin K (phytomenadione) and vitamin D3 (cholecalciferol).

Therefore the present invention also relates to a composition comprising (a) a core, wherein the core comprises at least one fat soluble compound chosen from the group consisting of vitamin A, vitamin A acetate, vitamin A palmitate, vitamin E, vitamin E acetate, vitamin K (phytomenadione), vitamin D3 (cholecalciferol), PUFA and carotenoids (such as α- or β-carotene, 8'-apo-β-carotenal, 8'-apo-β-carotenoic acid esters, canthaxanthin, astaxanthin, lycopene, lutein, zeaxanthin or crocetin), and (b) a coating system, comprising
 (i) at least one lipid compound and
 (ii) at least one gum chosen from the group consisting of gum acacia, gum ghatti and tic gums, and (iii) at least one film forming compound and/or at least one emulsifier, characterised in that the mass median diameter of the lipid compound is less than 1 μm.

In addition the core can comprise further ingredients, usually additives, which are used in the production of such compounds or additives which are useful for products in which the compositions according to the present invention are incorporated. The core of the composition can be in any form. It can for example be in the form of beadlet comprising the active ingredient. A suitable beadlet, which can be coated by the coating system according to the present invention can be found in WO 2007/045488.

Furthermore the composition according to present invention comprises
(a) 50 to 95 wt-%, based on the total weight of the composition, of core and
(b) 5 to 50 wt-%, based on the total weight of the composition, of coating system.

Furthermore the composition according to present invention comprises
(a) 50 to 95 wt-%, based on the total weight of the composition, of core comprising at least one fat soluble compound chosen from the group consisting of vitamin A, vitamin A acetate, vitamin A palmitate, vitamin E, vitamin E acetate, vitamin K (phytomenadione), vitamin D3 (cholecalciferol), PUFA and carotenoids (such as α- or β-carotene, 8'-apo-β-carotenal, 8'-apo-β-carotenoic acid esters, canthaxanthin, astaxanthin, lycopene, lutein, zeaxanthin or crocetin), and
(b) 5 to 50 wt-%, based on the total weight of the composition, of coating system comprising
  (i) 10 to 50 wt-%, based on the total weight of the coating system, of at least one lipid compound chosen from the group consisting of stearic acid or palmitic acid, as well as their salts and
  (ii) 5 to 30 wt-%, based on the total weight of the coating system, of at least one gum chosen from the group consisting of gum accacia, gum ghatti and tic gums, and
  (iii) 40 to 80 wt-%, based on the total weight of the coating system, of at least one film forming compound and/or at least one emulsifier chosen from the group consisting of alginates, pectins, guar gum, caroube gum, xanthan, starches, modified starches, cellulose, cellulose derivatives (like carboxymethylcellulose or hydroxypropylmethylcellulose), sucrose ester, ascorbyl palmitate and polyoxyethylene-sorbitan-fatty acid esters, and optionally
  (iv) 5 to 20 wt-%, based on the total weight of the coating system, of at least one plasticizer chosen from the group consisting of sugars (like sucrose), derivatives (mannitol, sorbitol), glycerol, mono- and diglyceride, acetylated monoglyceride, polyethylene glycol (PEG) and polypropylene glycol, and optionally
  (v) up to 5 wt-%, based on the total weight of the coating system, of at least one further ingredient chosen from the group consisting of dyestuffs, antioxidants, fillers, pH buffers and taste masking substances, characterised in that the mass median diameter of the lipid compound is less than 1 μm.

The composition as described above can optionally been further coated for example by a fat layer.

The coated (single coating or multiple coating) compositions according to the present invention can be used in any kind of formulations, wherein the use of such fat soluble ingredients is useful. Usually such compositions can be used in food products. The food products can be in any form.

The coated compositions according to the present invention can also be used in feed products for animals such as poultry, pigs, fish, ruminants, etc. The feed products can be in any form.

The compositions according to the present invention can also be used as or used in dietary supplements. The dietary supplements can be in any form.

The coated compositions according to the present invention can also be used in pharmaceutical products. The pharmaceutical products can be in any galenical form, usually in the form of tablets.

A further embodiment of the present invention relates to food products, feed products, dietary supplements and/or pharmaceutical products, comprising at least one coated composition as defined above.

The invention is illustrated by the following Example. All temperatures are given in ° C. and all parts and percentages are related to the weight.

EXAMPLE 1

Coated Particles Comprising Vitamin A

Step 1: Coating Formulation 100 g Hydroxypropylmethylcellulose (HPMC) type methocel E19 are added in 1550 g deionised water (80-90° C.) and left for about 1 hour. Then 40 g of gum acacia Senegal (Benecke) is added. The solution is then left overnight at room temperature for degassing. 676 g of the previous solution is heated up at 50-60° C. 24 g of stearic acid (Merck, "plant type") is added and mixed. The micronisation of the stearic acid is then ensured by a Polytron 6000 rotor stator system by 20000 rpm for 10 minutes. The quick cooling of the suspension is ensured by the addition of it in a 284 g of water/ice mixed (about 250 g ice and 34 g water). The final composition of the coating formulation is: 40 g HPMC, 24 g stearic acid, 16 g of gum acacia, 904 g of demineralised water.

The size of the particles of stearic acid in the suspension are measured with a Malvern Mastersizer 2000 with Ultrasound at $d3,2=0.144$ μm, $d10=0.075$ μm, $d50=0.17$ μm, $d90=0.83$ μm.

Step 2: Application of the Coating Formulation on the Core Surface 300 g of a beadlet Vitamin A form (as described in patent WO 2007/045488 and containing 38% Vitamin A acetate, 46% capsul HS, 11% sucrose, 5% silicic acid) is fluidised in a small laboratory fluid bed equipment (DMR, WFP mini) and used as Core particles. 194 g of the coating formulation obtained in the step 1 is sprayed on the surface of the beadlets with a 2-fluid nozzle (air pressure: 1.5 bars) in a bottom-spray configuration. The spraying time is of about 75 min with an inlet air temperature of 80° C. The final composition of the product obtained is:

TABLE 1

| Compound of Example 1 | |
|---|---|
| Ingredients | Wt-% |
| CORE (beadlets) | 95 |
| HPMC | 2.5 |
| Gum acacia | 1.0 |
| Stearic acid | 1.5 |

EXAMPLE 2

Coated Particles Comprising Vitamin A

Step 1: Coating Formulation 100 g Hydroxypropylmethylcellulose (HPMC) type methocel E19 are added in 1300 g deionised water (80-90° C.) and left for about 1 hour. Then 40 g of gum acacia Senegal (Benecke) is added. The solution is then left overnight at room temperature for degassing. 60 g of stearic acid (Merck, "plant type") is added and mixed. The micronisation of the stearic acid is then ensured by a Polytron 6000 rotor stator system by 20000 rpm for 60 minutes. The quick cooling of the suspension is ensured by the addition of it in a 500 g of water/ice mixed (about 450 g ice and 50 g water). Finally, 96 g of deionised water are added. The final composition of the coating formulation is: 100 g HPMC, 60 g stearic acid, 40 g of gum acacia, 1800 g of demineralised water.

The size of the particles of stearic acid in the suspension are measured with a Malvern Mastersizer 2000 at d3,2=0.163 μm, d10=0.078 μm, d50=0.19 μm, d90=7.3 μm.

Step 2: Application of the Coating Formulation on the Core Surface 300 g of a beadlet Vitamin A form (as described in patent WO 2007/045488 and containing 26% Vitamin A acetate, 1% of mixed tocopherol, 55% capsul HS, 14% fructose, 4% starch) is fluidised in a small laboratory fluid bed equipment (DMR, WFP mini) and used as Core particles. 410 g of the coating formulation obtained in the step 1 is sprayed on the surface of the beadlets with a 2-fluid nozzle (air pressure: 1.5 bars) in a top-spray configuration. The spraying time is of about 157 min with an inlet air temperature of 80° C.

50 g of the obtained product is then mixed with 9 g stearic acid plant (Merck) and heated up to 75° C. for 10 minutes. The product is then cooled to RT by mixing. The final composition of the product obtained is:

TABLE 2

| Compound of Example 2 | |
|---|---|
| Ingredients | Wt-% |
| CORE (beadlets) | 74.6 |
| HPMC | 5.1 |
| Gum acacia | 2.0 |
| Stearic acid micronised | 3.1 |
| Stearic acid pure as additional layer | 15.2 |

Retention in typical feed premix composition at 25° C., 80% r.H. after 3 months
Rovimix® A 500 WS (non coated form) 30%
Compound of example 2 86.3%

EXAMPLE 3

Coated Particles Comprising PUFA

Step 1: Coating Formulation 156 g Hydroxypropylmethylcellulose (HPMC) type methocel E7 are added in 1044 g deionised water (80-90° C.) and left for about 1 hour. The solution is then left overnight at room temperature for degassing. In 1031 g of the previous solution 36 g of stearic acid (Merck, "plant type") is added and mixed. The micronisation of the stearic acid is then ensured by a Polytron 6000 rotor stator system by 18000 rpm for 20 minutes. The quick cooling of the suspension is ensured by the addition of 150 g of cold water. In 1015 g of the solution, 310 g of ice/water mix (250 g ice/60 g water) is added. Then 26 g gum acacia is added and stirred until dissolved. The final composition of the coating formulation is: 112 g HPMC, 30 g stearic acid, 26 g of gum acacia, 1183 g of demineralised water.

The size of the particles of stearic acid in the suspension are measured with a Coulter N4 Plus at a mean diameter of 0.496 μm.

Step 2: Application of the Coating Formulation on the Core Surface 428.6 g Ropufa® '10' n-3 INF Powder are mixed with 71.4 g stearic acid plant (Merck) and heated up to 55-60° C. for 30 minutes. The mix is then cooled down to RT while mixing.

250 g of the mix is fluidised in a small laboratory fluid bed equipment (DMR, WFP mini) and used as Core particles. 200 g of the coating formulation obtained in the step 1 is sprayed on the surface of the beadlets with a 2-fluid nozzle (air pressure: 1.5 bars) in a top-spray configuration. The spraying time is of about 121 min with an inlet air temperature of 55° C.

The final composition of the product obtained is:

TABLE 3

| Compound of Example 3 | |
|---|---|
| Ingredients | Wt-% |
| CORE (Ropufa + stearic acid) | 91 |
| HPMC | 6 |
| Gum acacia | 1.4 |
| Stearic acid micronised | 1.6 |

The sensory of these particles were evaluated by sniff test. Sniff test consists in presenting the forms to a panel of judges, ask them to sniff the products and then rate some given characteristics (sensory descriptors), by the use of an arbitrary scale. In this case it was used a scale from 1 to 7 (1 means the absence of fishiness and 7 an extremely high presence of the fishiness).

Ropufa® '10' n-3 INF Powder (non coated form)
Between slightly fishy (level 3) and middle intense fishy (level 4)
Compound of Example 3
Between not detectable (level 1) and very slightly fishy (level 2)

EXAMPLE 4

Coated Particles Comprising Vitamin A

Step 1: Coating Formulation
Same coating formulation as in example 1.
Step 2: Application of the Coating Formulation on the Core Surface 300 g of a beadlet Vitamin A form (as described in patent WO 2007/045488 and containing 26% Vitamin A, 45% gum acacia senegal, 19% maltodextrin, 10% starch) is fluidised in a small laboratory fluid bed equipment (DMR, WFP mini) and used as Core particles. 270 g of the coating formulation obtained in the step 1 is sprayed on the surface of the beadlets with a 2-fluid nozzle (air pressure: 1.5 bars) in a bottom-spray configuration. The spraying time is of about 105 min with an inlet air temperature of 80° C. 50 g of the obtained product is then mixed with 16.7 g of candelilla wax and heated up to 80° C. for 20 minutes. The mixed is then cooled to RT by mixing.

The final composition of the product obtained is:

TABLE 4

Compound of Example 4

| Ingredients | Wt-% |
|---|---|
| CORE | 69.9 |
| HPMC | 2.6 |
| Gum acacia | 1.0 |
| Stearic acid micronised | 1.5 |
| Candelilla wax | 25 |

The invention claimed is:

1. A coating system comprising:
   (i) an aqueous solution comprising (ia) at least one gum having emulsifying properties selected from the group consisting of gum acacia, gum ghatti and tic gums, and (ib) at least one film forming compound consisting of carboxymethylcellulose and/or hydroxypropylmethylcellulose, and
   (ii) powder particles having a mass median diameter which is less than 1 µm of at least one lipid compound which is selected from the group consisting of saturated fatty acids and salts thereof which are suspended in the aqueous solution (i).

2. The coating system according to claim 1, wherein the mass median diameter of the powder particles of the least one lipid compound is less than 0.8 µm.

3. The coating system according to claim 1, further comprising at least one emulsifier selected from the group consisting of sucrose ester, ascorbyl palmitate and polyoxyethylene-sorbitan-fatty acid esters.

4. The coating system according to claim 1, which further comprises (iv) at least one plasticizer.

5. The coating system according to claim 1, wherein the at least one lipid compound is present in an amount of 10 to 50 wt. %, based on total weight of the coating system.

6. The coating system according to claim 1, wherein the at least one gum having emulsifying properties is present in an amount of 5 to 30 wt. %, based on total weight of the coating system.

7. The coating system according to claim 1, wherein the at least one film forming compound is present in an amount of 40 to 80 wt. %, based on total weight of the coating system.

8. The coating system according to claim 4, wherein the at least one plasticizer is present in an amount of 5 to 20 wt. %, based on total weight of the coating system, and wherein the plasticizer is at least one selected from the group consisting of sugars, mannitol, sorbitol, glycerol, mono- and diglyceride, acetylated monoglyceride, polyethylene glycol (PEG) and polypropylene glycol.

9. The coating system according to claim 1, further comprising at least one further ingredient in an amount of up to 5 wt. %, based on total weight of the coating system, which is selected from the group consisting of dyestuffs, antioxidants, fillers, pH buffers and taste masking substances.

10. The coating system according to claim 5, wherein the at least one lipid compound is present in an amount of 20 to 40 wt-%, based on the total weight of the coating system.

11. The coating system according to claim 6, wherein the at least one gum having emulsifying properties is present in an amount of 10 to 25 wt. %, based on the total weight of the coating system.

12. The coating system according to claim 7, wherein the at least one film forming compound is present in an amount of 45 to 70 wt. %, based on the total weight of the coating system.

13. The coating system according to claim 8, wherein the at least one plasticizer comprises sucrose.

14. A coating system comprising powder particles of stearic acid having a mass median diameter of less than 1 µm which are suspended in an aqueous solution comprising (a) gum acacia, and (b) hydroxypropylmethylcellulose.

15. The coating system according to claim 14, wherein the mass median diameter of the powder particles of stearic acid is less than 0.8 µm.

16. The coating system according to claim 14, wherein the coating system comprises, based on total weight of the coating system:
   (i) 10 to 50 wt. % of the stearic acid,
   (ii) 5 to 30 wt. % of the gum acacia, and
   (iii) 40 to 80 wt. % of the hydroxypropylmethylcellulose.

17. A composition comprising:
   (a) a core which comprises at least one fat soluble compound; and
   (b) a coating system according to claim 1 surrounding the core.

18. The composition according to claim 17, wherein the fat soluble compound is at least one selected from the group consisting of vitamin A, vitamin A acetate, vitamin A palmitate, vitamin E, vitamin E acetate, vitamin K, vitamin D3, polyunsaturated fatty acids (PUFA) and carotenoids.

19. The composition according to claim 17, comprising, based on total weight of the composition:
   (a) 50 to 95 wt. % of the core; and
   (b) 5 to 50 wt. % of the coating system.

20. A food product, feed product, dietary supplement and/or pharmaceutical product, comprising the composition according claim 17.

* * * * *